(12) United States Patent
McLean

(10) Patent No.: US 8,409,134 B2
(45) Date of Patent: Apr. 2, 2013

(54) POWER INJECTOR HAVING CALIBRATED PRESSURE MONITORING FUNCTIONALITY

(75) Inventor: Mike W. McLean, Liberty Township, OH (US)

(73) Assignee: Mallinckrodt LLC, Hazelwood, MO (US)

(*) Notice: Subject to any disclaimer, the term of this patent is extended or adjusted under 35 U.S.C. 154(b) by 90 days.

(21) Appl. No.: 13/055,764

(22) PCT Filed: Aug. 21, 2009

(86) PCT No.: PCT/US2009/054555
§ 371 (c)(1),
(2), (4) Date: Jan. 25, 2011

(87) PCT Pub. No.: WO2010/027695
PCT Pub. Date: Mar. 11, 2010

(65) Prior Publication Data
US 2011/0137251 A1 Jun. 9, 2011

Related U.S. Application Data

(60) Provisional application No. 61/091,757, filed on Aug. 26, 2008.

(51) Int. Cl.
*A61M 31/00* (2006.01)

(52) U.S. Cl. .......... 604/67; 604/151
(58) Field of Classification Search .......... 604/151–154, 604/65–67; 73/1.36; 702/100; 600/432
See application file for complete search history.

(56) References Cited

U.S. PATENT DOCUMENTS

| | | | |
|---|---|---|---|
| 5,425,716 A | 6/1995 | Kawasaki et al. | |
| 6,368,314 B1 | 4/2002 | Kipfer et al. | |
| 6,673,033 B1 * | 1/2004 | Sciulli et al. | 604/67 |
| 2005/0049556 A1 | 3/2005 | Tanaka | |
| 2006/0213249 A1 * | 9/2006 | Uram et al. | 73/1.36 |
| 2010/0305506 A1 * | 12/2010 | Fahrer | 604/118 |

\* cited by examiner

*Primary Examiner* — Theodore Stigell
(74) *Attorney, Agent, or Firm* — Marsh Fischmann & Breyfogle LLP

(57) ABSTRACT

Control logic (110) for a power injector is disclosed, where this power injector control logic (110) includes a syringe fill protocol (114), a pressure calibration protocol (116), a pressure monitoring protocol (118), and an injection protocol (120). The power injector control logic (110) is configured to execute the pressure calibration protocol (116) on each execution of the syringe fill protocol (114). The pressure calibration protocol (116) updates the pressure monitoring protocol (118), which is executed during execution of the injection protocol (120).

35 Claims, 9 Drawing Sheets

POWER INJECTOR HAVING CALIBRATED PRESSURE MONITORING FUNCTIONALITY

RELATED APPLICATIONS

This application claims priority to U.S. Provisional Patent Application No. 61/091,757 filed on 26 Aug. 2008 entitled "POWER INJECTOR HAVING CALIBRATED PRESSURE MONITORING FUNCTIONALITY".

FIELD OF THE INVENTION

The present invention generally relates to the field of power injectors and, more particularly, to monitoring and/or controlling pressures associated with power injector operations.

BACKGROUND

Various medical procedures require that one or more medical fluids be injected into the patient. Medical imaging procedures oftentimes involve the injection of a contrast media into the patient, possibly along with saline or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

At least certain injection procedures will incorporate one or more pressure limits. A power injector may be configured to undertake one or more actions in response to a pressure limit having been met or exceeded. In many cases, a pressure of a fluid discharge from the power injector is monitored/determined, and is then compared with one or more pressure limits. The accurateness of the pressure value that is compared with a pressure limit will of course influence the accuracy of the power injectors pressure-monitoring capabilities.

Pressure in the syringe may be calculated by determining the force to push the plunger and dividing that force by the effective surface area of the syringe plunger. The force to push the plunger can be acquired by various methods, including direct reading from a load-cell or the like or a drive motor power calculation using voltage and current. These methods have inherent variations and need to be calibrated and the zero point needs to be set. This is generally done at the factory during assembly and sometimes adjusted by service personnel. Variables that impact the zero point may include ambient temperature, injector wear, line voltage, and manufacturing variations in the syringe.

SUMMARY

A first aspect of the present invention is embodied by a method of operation for a power injector. A syringe that includes a syringe plunger is installed on a power injector. This installation occurs when the syringe is in an empty state (e.g., no fluid intended for injection into a patient is contained within the syringe when installed). Using the power injector, fluid is loaded into the syringe and is thereafter discharged from the syringe. A pressure monitoring protocol of the injector is calibrated each time a syringe is installed on the power injector and prior to any fluid being discharged from the syringe. The fluid discharge from the syringe is monitored using the pressure monitoring protocol.

A second aspect of the present invention is embodied by a method of operation for a power injector. A syringe that includes a syringe plunger is installed on the power injector. This installation occurs when the syringe is in an empty state (e.g., no fluid intended for injection into a patient is contained within the syringe when installed). While the syringe is installed on the power injector, a fluid loading operation is undertaken in relation to the syringe. In this fluid loading operation, the syringe plunger is advanced within the syringe while the syringe is in the empty state. In addition, a pressure monitoring protocol is calibrated based at least in part upon this advancement of the syringe plunger within the syringe. Subsequently, a fluid (e.g., contrast media, saline, or a combination thereof) is loaded into the syringe. The fluid is thereafter discharged from the syringe with the fluid discharge being monitored using the pressure monitoring protocol.

A third aspect of the present invention is embodied by a method of operation for a power injector. A syringe that includes a syringe plunger is installed on the power injector. This installation occurs when the syringe is in an empty state (e.g., no fluid intended for injection into a patient is contained within the syringe when installed). While the syringe is installed on the injector, a fill sequence is initiated in relation to the syringe. This fill sequence includes moving the syringe plunger within the syringe while the syringe remains in its empty state (a first moving step) and acquiring a reference value from this first moving step. In addition, the fill sequence includes loading a fluid into the syringe; this includes moving the syringe plunger within the syringe (a second moving step). Fluid is thereafter discharged from the syringe by moving the syringe plunger within the syringe (a third moving step). This fluid discharge is monitored using the reference value acquired from executing the noted fill sequence.

A number of feature refinements and additional features are applicable to the third aspect of the present invention. These feature refinements and additional features may be used individually or in any combination. The reference value acquired during the execution of the fill sequence may be in the form of a force that is required to move the syringe plunger when the syringe is in an empty state. Monitoring the fluid discharge may entail comparing a pressure limit with a pressure associated with the fluid discharge, where this comparison accounts for the noted reference value. In one embodiment, the monitoring of the fluid discharge entails monitoring a pressure associated with the fluid discharge, identifying a calibrated pressure, and comparing this calibrated pressure with a pressure limit. The calibrated pressure may be based upon reducing a monitored pressure value by a pressure value that relates to or is based upon the reference value.

A number of feature refinements and additional features are applicable to each of the first, second, and third aspects of the present invention. These feature refinements and additional features may be used individually or in any combination. The following discussion is applicable to each of the first, second, and third aspects, up to the start of a discussion on a fourth aspect of the present invention.

Any appropriate fluid (e.g., including a single fluid or any combination of multiple fluids) may be loaded into or provided to the syringe in any appropriate manner when installed on the power injector. It should be appreciated that even though directing fluid into a syringe may be characterized as a "fill operation" or the like, this does not require that a maximum fluid volume needs to be directed into the syringe for a subsequent fluid discharge. Any appropriate fluid volume may be directed into a syringe installed on the power injector, whether this is characterized as a loading operation, a fill operation, or the like.

In one embodiment, a fluid source is fluidly interconnected with the syringe after being installed on the power injector. The syringe plunger then may be retracted to "draw" fluid into the syringe (e.g., via suction or vacuum forces), the syringe plunger may be retracted to provide a volume for receiving a fluid quantity within the syringe, (e.g., such that gravitational forces at least assist in directing a fluid flow into the syringe), or both. It may be such that the syringe plunger is in an at least partially retracted state when initially installed on the power injector. In this case, the syringe plunger may be advanced toward a discharge nozzle of the syringe. Data may be acquired during this advancement of the syringe plunger for calibrating a pressure monitoring protocol. With the syringe plunger being in an extended state (e.g., at or toward a syringe discharge nozzle), the syringe plunger then may be retracted (e.g., via a movement of the syringe plunger in an opposite direction) to load fluid into or to accommodate the loading of fluid into the syringe.

Calibration of a pressure monitoring protocol of the power injector may entail advancing the plunger while the syringe is in an empty state. This movement of the syringe plunger may be part of a fluid loading operation or fill sequence for the installed syringe. In one embodiment, calibration of a pressure monitoring protocol entails determining a force required to move the plunger when the syringe is in an empty state. Further characterizations apply to a movement of the syringe plunger for calibration purposes. Advancement of the syringe plunger for calibration purposes may be initiated with the syringe plunger being a fully retracted position. In one embodiment, the syringe includes a discharge nozzle. The syringe plunger may be advanced in a direction for calibration purposes such that the spacing between the syringe plunger and the discharge nozzle is decreased, such that the syringe plunger moves toward or in the direction of the discharge nozzle, or both.

Calibration of the pressure monitoring protocol may be undertaken after the syringe has been installed on the power injector, prior to loading or directing fluid into the syringe, or both. The pressure monitoring protocol may require a zero-pressure reference value, and the calibration of the pressure monitoring protocol may provide this zero-pressure reference value. In one embodiment, this calibration entails determining a magnitude of a force required to advance the syringe plunger when the syringe is in an empty state. This force or a related value may be subtracted from a monitored pressure value to define a calibrated pressure or calibrated pressure value. This calibrated pressure may be compared with one or more pressure limits for purposes of monitoring a fluid discharge from the syringe by operation of the power injector.

Fourth through sixth aspects of the present invention are each embodied by a power injector that includes a syringe plunger driver, a syringe, and power injector control logic. The syringe plunger driver includes a motorized drive source, and the syringe includes a syringe plunger for each of the fourth through the sixth aspects.

In the case of the fourth aspect of a power injector of the above-noted configuration, the power injector control logic includes a syringe fill protocol and a pressure monitoring protocol. The pressure monitoring protocol incorporates a pressure calibration factor. The power injector control logic is configured to update this pressure calibration factor in relation to each execution of the syringe fill protocol—there is a one-to-one relation between updating the pressure calibration factor and each execution of the syringe fill protocol.

In the case of the fifth aspect of a power injector of the above-noted configuration, the power injector control logic includes a syringe fill protocol, a pressure calibration protocol, and a pressure monitoring protocol. The pressure calibration protocol is operatively interconnected with the pressure monitoring protocol. The power injector control logic is configured to execute the pressure calibration protocol in relation to each execution of the syringe fill protocol—there is a one-to-one relation between each execution of the pressure calibration protocol and each execution of the syringe fill protocol.

In the case of the sixth aspect of a power injector of the above-noted configuration, the power injector control logic includes a syringe fill protocol, a pressure calibration protocol, and a pressure monitoring protocol. The pressure calibration protocol is operatively interconnected with the pressure monitoring protocol. The power injector further includes a syringe fill protocol trigger that is operatively interconnected with each of the syringe fill protocol and the pressure calibration protocol.

A number of feature refinements and additional features are applicable to each of the fourth, fifth, and sixth aspects of the present invention. These feature refinements and additional features may be used individually or in any combination. The following discussion is separately applicable to each of the fourth, fifth, and sixth aspects.

The power injector may include a pressure monitoring protocol, which in turn utilizes a pressure calibration factor. The power injector control logic may be configured to update this pressure calibration factor in relation to each execution of the syringe fill protocol—there is a one-to-one relation between updating the pressure calibration factor and each execution of the syringe fill protocol. The syringe fill protocol may be configured to advance the syringe plunger with the syringe being an empty state. In one embodiment, the noted pressure calibration factor is based upon data acquired from this advancement of the syringe plunger.

The power injector may include a syringe fill protocol trigger. This syringe fill protocol trigger may be in the form of or result from information received from one or more sensors of the injector based on information from the syringe (e.g., RFID data tag, bar code, detents, outcroppings, optically detectable markings or the like of the syringe being identified by an appropriate sensor of the power injector) that are associated with an "empty" syringe having been installed on the power injector. A syringe fill sequence may be automatically initiated in response to the power injector identifying that an empty syringe has been installed on the power injector. The syringe fill protocol trigger could also be in the form of a hand-activated device of any appropriate type. In one embodiment, the syringe fill protocol trigger is presented on a touch screen display, graphical user interface, or the like associated with the power injector (e.g., on a powerhead of the power injector) and is responsive to user input. As such, the above-noted hand-activated device may be in the form of a button or the like on a touch screen display or graphical user interface for the power injector. A user may activate such a button to initiate a manual fill of the syringe or an automatic fill of the syringe.

A number of feature refinements and additional features are separately applicable to each of above-noted first, second, third, fourth, fifth, and sixth aspects of the present invention. These feature refinements and additional features may be used individually or in any combination in relation to each of the first, second, third, fourth, fifth, and sixth aspects. Initially, any feature that is intended to be limited to a "singular" context or the like will be clearly set forth herein by terms such as "only," "single," "limited to," or the like. Merely introducing a feature in accordance with commonly accepted antecedent basis practice (or failing to utilize the phrase "at least one" or the like in relation to a given feature) does not limit the corresponding feature to the singular (e.g., indicating that a power injector includes "a syringe" alone does not mean that the power injector includes only a single syringe). Finally, use of the phrase "at least generally" or the like in relation to a particular feature encompasses the corresponding characteristic and insubstantial variations thereof (e.g., indicating that a syringe barrel is at least generally cylindrical encompasses the syringe barrel being cylindrical).

Any "logic" that may be utilized by any of the various aspects of the present invention, including without limitation each protocol incorporated by any such logic, may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. This logic may be implemented at any single location or at multiple locations that are interconnected in any appropriate manner (e.g., via any type of network).

The power injector may be of any appropriate size, shape, configuration, and/or type. The power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading of fluid or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more powered drive sources of any appropriate size, shape, configuration, and/or type. Multiple powered drive source outputs may be combined in any appropriate manner to advance a single syringe plunger at a given time. One or more powered drive sources may be dedicated to a single syringe plunger driver, one or more powered drive sources may be associated with multiple syringe plunger drivers (e.g., incorporating a transmission of sorts to change the output from one syringe plunger to another syringe plunger), or a combination thereof. Representative powered drive source forms include a brushed or brushless electric motor, a hydraulic motor, a pneumatic motor, a piezoelectric motor, or a stepper motor.

The power injector may be used for any appropriate application where the delivery of one or more medical fluids is desired, including without limitation any appropriate medical application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging). The power injector may be used in conjunction with any component or combination of components, such as an appropriate imaging system (e.g., a CT scanner). For instance, information could be conveyed between the power injector and one or more other components (e.g., scan delay information, injection start signal, injection rate).

Any appropriate number of syringes may be utilized by power injector and in any appropriate manner (e.g., detachably; front-loaded; rear-loaded; side-loaded), any appropriate medical fluid may be discharged from a given syringe of the power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit (e.g., medical tubing set), where this conduit is fluidly interconnected with the syringe in any appropriate manner and directs fluid to a desired location (e.g., to a catheter that is inserted into a patient, for instance for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a syringe plunger that is disposed within and movable relative to the syringe barrel. This syringe plunger may interface with a syringe plunger driver such that the syringe plunger driver is able to advance the syringe plunger in at least one direction, and possibly in two different, opposite directions (e.g., an extension and retraction of the syringe plunger driver).

Each of the various aspects of the present invention may be characterized as taking into account various variables that may impact the zero pressure point, and resetting the zero point for each syringe during the filling cycle rather than relying on a setting made under different conditions (e.g., at the factory). For instance, the various aspects of the present invention may be characterized as recalibrating the zero pressure point to compensate for one or more of ambient temperature, input line voltages, injector wear, and syringe variations.

Each of the various aspects of the present invention may be characterized as an initialization of a pressure-monitoring functionality utilized by a power injector. A power injector may utilize a pressure-monitoring functionality for any appropriate purpose. For instance, a pressure-monitoring functionality may be utilized for extravasation detection, to determine if an empty syringe is installed on the power injector, for error detection (e.g., to attempt to identify errors that may occur in the execution of an injection protocol), to enable detection of air injections, or the like. The enhanced accuracy of a pressure-monitoring functionality that may be realized by the present invention may be of particular benefit at lower operating pressures (e.g., when operating a power injector to provide a lower flow rate for injection into a patient), when using lower pressure-rated I.V. access devices, or both. For instance, the present invention may have particular applicability at injections pressures of 50 psi or lower.

DETAILED DESCRIPTION

Figure 1:
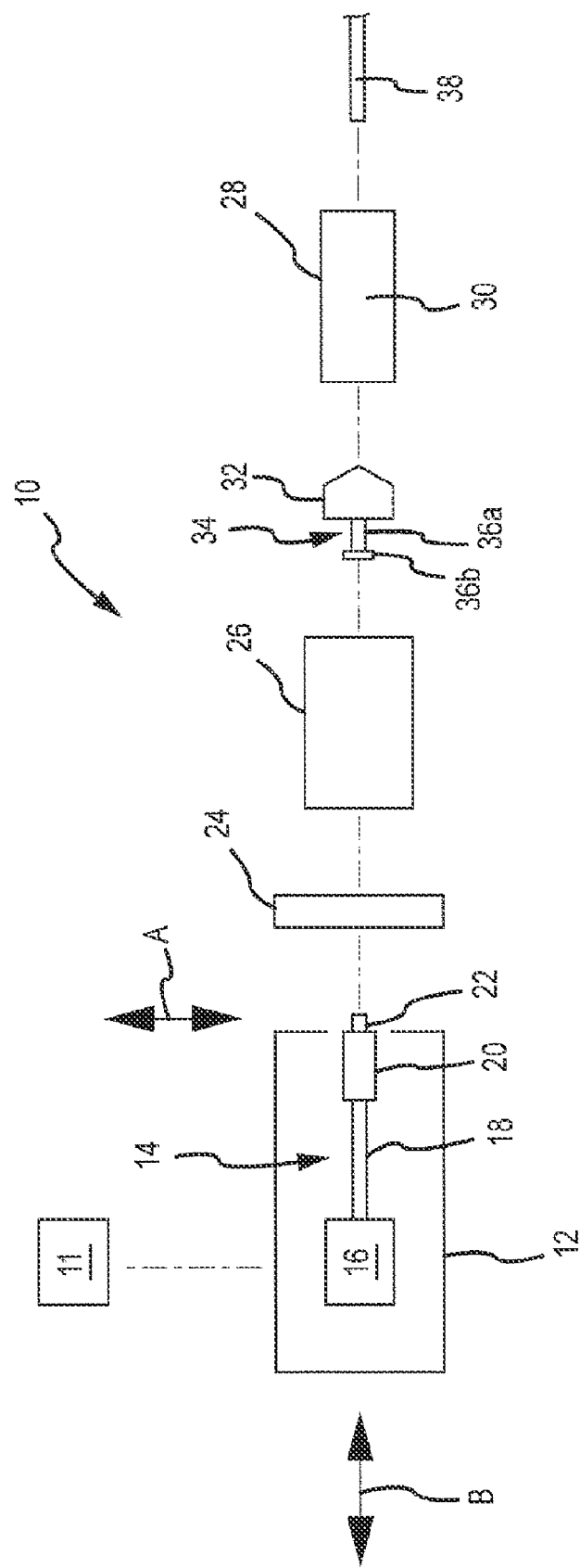
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide one or any combination of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on this powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a powered drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, it may such that these components may or may not be coupled when the ram 20 advances the syringe plunger 32 to discharge fluid from the syringe 28 (e.g., the ram 20 may simply "push on" the syringe plunger coupler 34 or on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
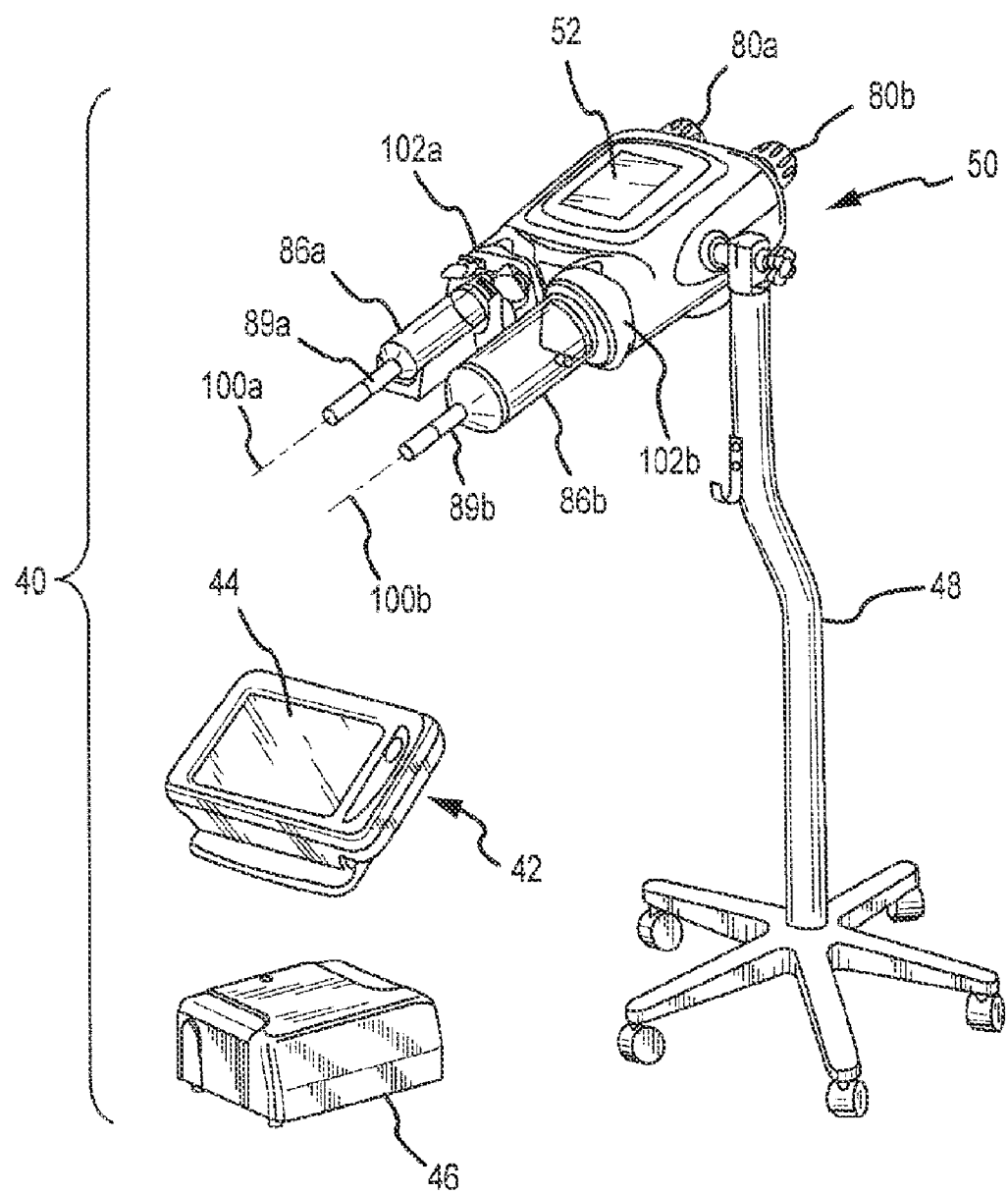
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 is mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one or more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
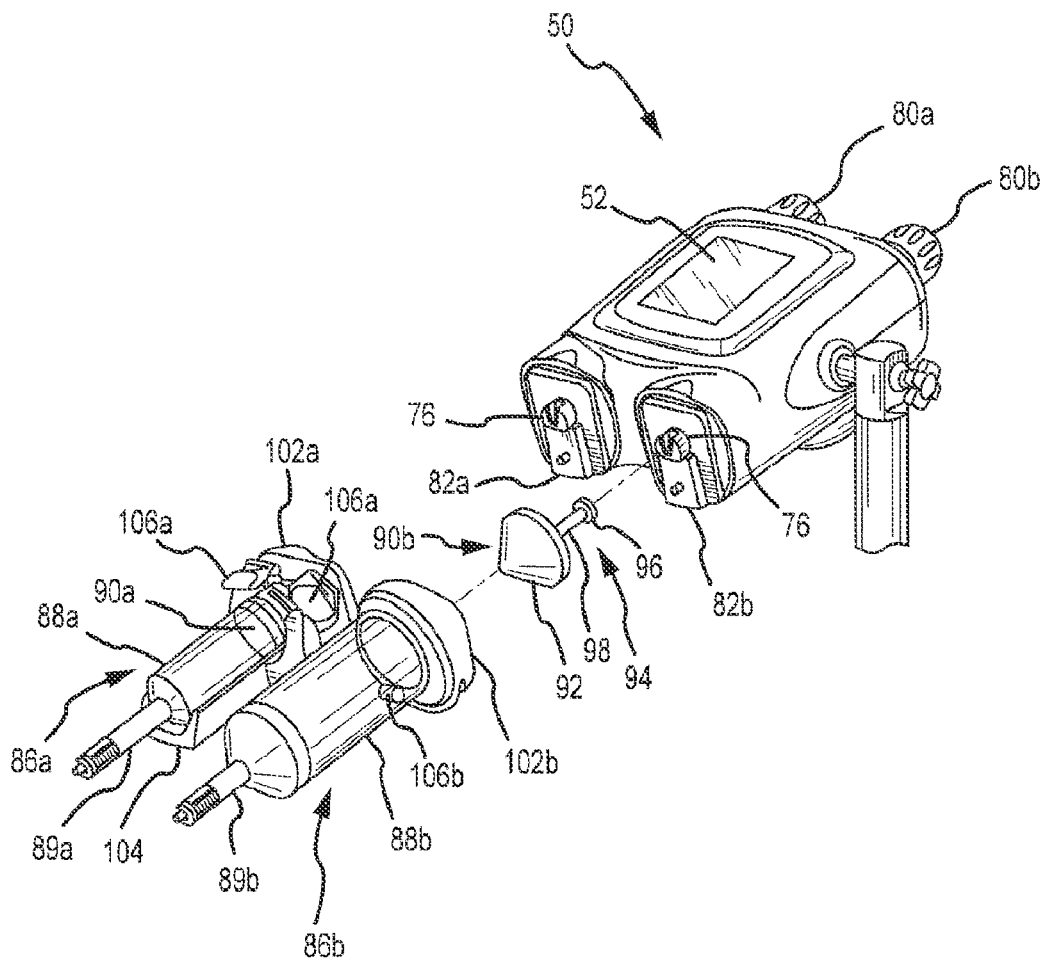
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within a syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b along an axis 100b (FIG. 2A) via operation of the powerhead 50 will discharge fluid from within the syringe barrel 88b through a nozzle 89b of the syringe 86b. An appropriate conduit (not shown) will typically be fluidly interconnected with the nozzle 89b in any appropriate manner to direct fluid to a desired location (e.g., a patient).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74 (FIG. 2C), which are each part of a syringe plunger drive assembly or syringe plunger driver 56

(FIG. 2C) for the syringe 86a, is positioned in proximity to the faceplate 102a when mounted on the powerhead 50. Details regarding the syringe plunger drive assembly 56 will be discussed in more detail below in relation to FIG. 2C. Generally, the ram coupler 76 may be coupled with the syringe plunger 90a of the syringe 86a, and the ram coupler 76 and ram 74 (FIG. 2C) may then be moved relative to the powerhead 50 to move the syringe plunger 90a along the axis 100a (FIG. 2A). It may be such that the ram coupler 76 is engaged with, but not actually coupled to, the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 86a at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 for interfacing with the faceplate 102b. A ram coupler 76 of a ram 74 (FIG. 2C), which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 2C. Generally, the ram coupler 76 may be coupled with the syringe plunger 90b of the syringe 86b, and the ram coupler 76 and ram 74 (FIG. 2C) may be moved relative to the powerhead 50 to move the syringe plunger 90b along the axis 100b (FIG. 2A). It may be such that the ram coupler 76 is engaged with, but not actually coupled to, the syringe plunger 90b when moving the syringe plunger 90b to discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102b on and remove the faceplate 102b from its mounting 82b on the powerhead 50. The faceplate 102b also may be used to couple the syringe plunger 90b with its corresponding ram coupler 76 on the powerhead 50. In this regard, the faceplate 102b may include a handle 106b. Generally and with the syringe 86b being initially positioned within the faceplate 102b, the syringe 86b may be rotated along its long axis 100b (FIG. 2A) and relative to the faceplate 102b. This rotation may be realized by moving the handle 106b, by grasping and turning the syringe 86b, or both. In any case, this rotation moves/translates both the syringe 86b and the faceplate 102b at least generally within a plane that is orthogonal to the axes 100a, 100b (associated with movement of the syringe plungers 90a, 90b, respectively, and illustrated in FIG. 2A). Rotating the syringe 86b in one direction moves/translates the syringe 86b and faceplate 102b in an at least generally downward direction to couple the syringe plunger 90b with its corresponding ram coupler 76. Rotating the syringe 86b in the opposite direction moves/translates the syringe 86b and faceplate 102b in an at least generally upward direction to uncouple its syringe plunger 90b from its corresponding ram coupler 76.

As illustrated in FIG. 2B, the syringe plunger 90b includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90b and its corresponding ram coupler 76 are in a coupled state or condition. The syringe plunger 90a may include a similar syringe plunger coupler 94 for interfacing with its corresponding ram coupler 76.

Figure 2C:
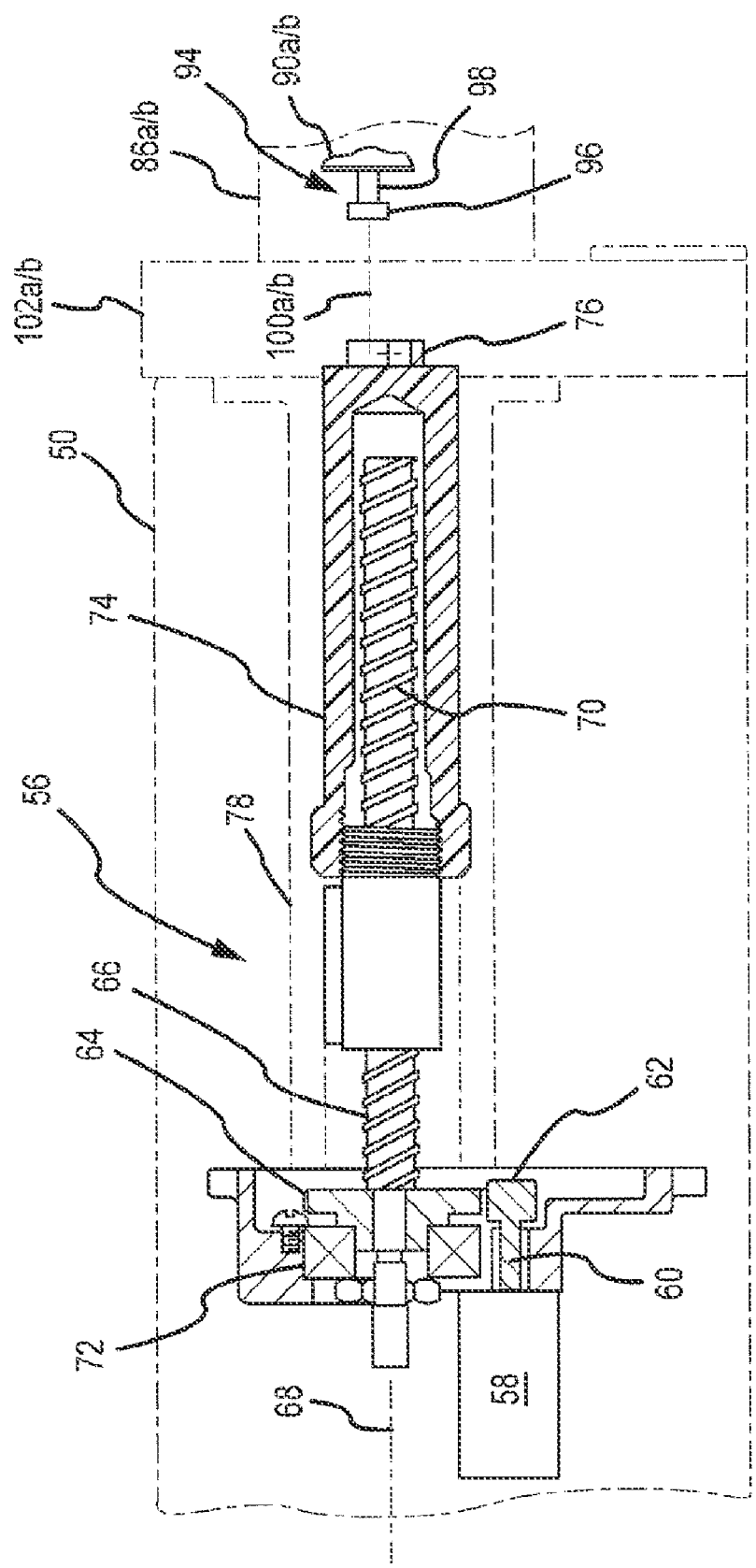
FIG. 2C is a schematic of one embodiment of a syringe plunger drive assembly used by the power injector of FIG. 2A.

The powerhead 50 is utilized to discharge fluid from the syringes 86a, 86b in the case of the power injector 40. That is, the powerhead 50 provides the motive force to discharge fluid from each of the syringes 86a, 86b. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86a, 86b. A separate syringe plunger drive assembly 56 may be incorporated into the powerhead 50 for each of the syringes 86a, 86b. In this regard and referring back to FIGS. 2A-B, the powerhead 50 may include hand-operated knobs 80a and 80b for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86a/b. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90a/b of the corresponding syringe 86a/b. When the ram coupler 76 and syringe plunger coupler 94 are appropriately coupled, the syringe plunger 90a/b moves along with ram 74. FIG. 2C illustrates a configuration where the syringe 86a/b may be moved along its corresponding axis 100a/b without being coupled to the ram 74. When the syringe 86a/b is moved along its corresponding axis 100a/b such that the head 96 of its syringe plunger 90a/b is aligned with the ram coupler 76, but with the axes 68 still in the offset configuration of FIG. 2C, the syringe 86a/b may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation computed tomography or CT imaging, magnetic resonance imaging or MRI, single photon emission computed tomography or SPECT imaging, positron emission tomography or PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

The power injectors 10, 40 of FIGS. 1 and 2A-C may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading of fluid or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more powered drive sources of any appropriate size, shape, configuration, and/or type. Multiple powered drive source outputs may be combined in any appropriate manner to advance a single syringe plunger at a given time. One or more powered drive sources may be dedicated to a single syringe plunger driver, one or more powered drive sources may be associated with multiple syringe plunger drivers (e.g., incorporating a transmission of sorts to change the output from one syringe plunger to another syringe plunger), or a combination thereof. Representative powered drive source forms include a brushed or brushless electric motor, a hydraulic motor, a pneumatic motor, a piezoelectric motor, or a stepper motor.

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

Figure 3:
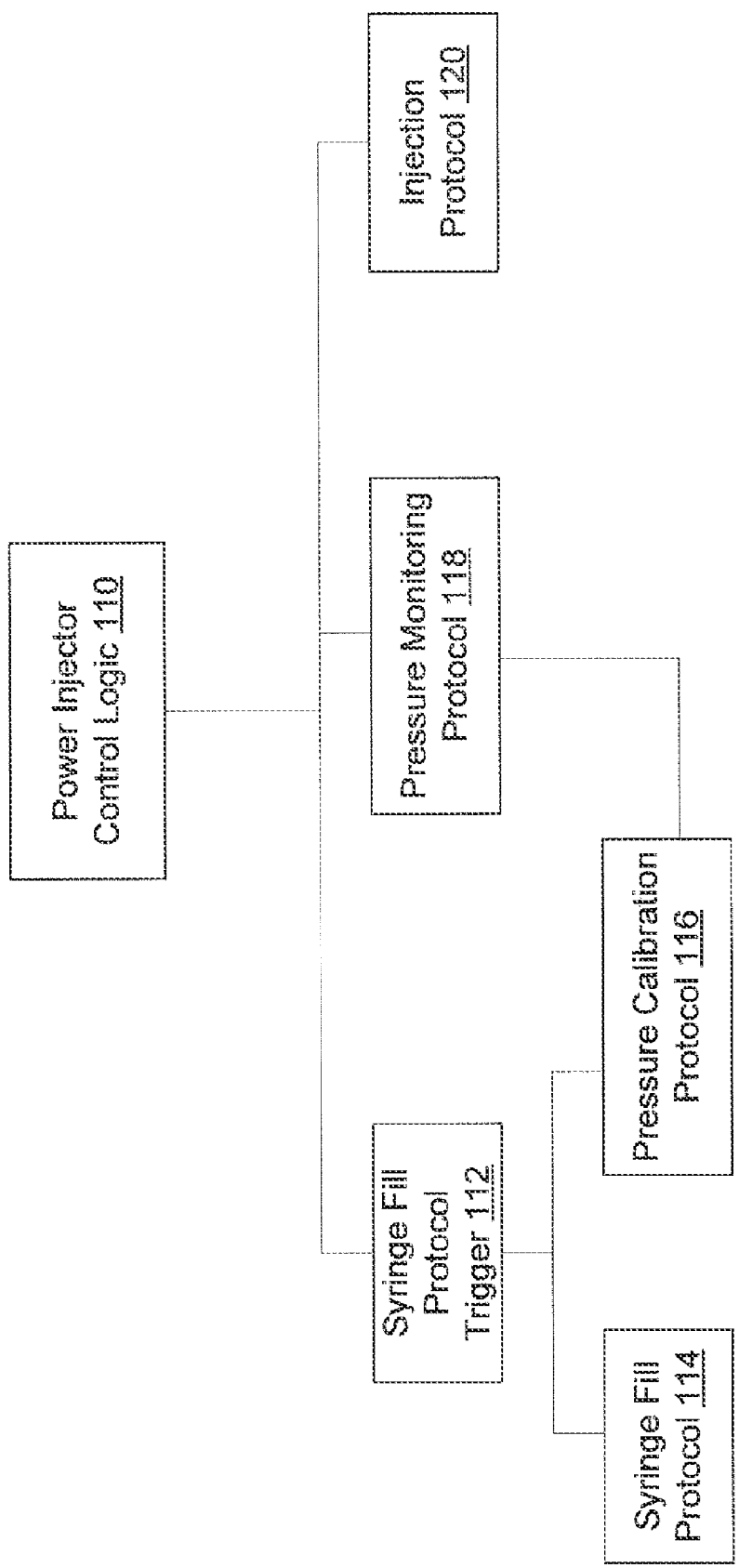
FIG. 3 is a functional schematic of one embodiment of power injector control logic that may be utilized by a power injector.

One embodiment of a power injector control logic or module is illustrated in FIG. 3 and identified by reference numeral 110. The power injector control logic 110 may be used by any appropriate power injector, including without limitation by each of the power injectors 10, 40 discussed above. Components of the power injector control logic 110 include a syringe fill protocol trigger 112, a syringe fill protocol 114, a pressure calibration protocol 116, a pressure monitoring protocol 118, and a fluid delivery or injection protocol 120.

The syringe fill protocol trigger 112 is operatively interconnected with each of the syringe fill protocol 114 and the pressure calibration protocol 116. Generally, the syringe fill protocol trigger 112 is used to initiate each of the syringe fill protocol 114 and the pressure calibration protocol 116. Stated another way, each of the syringe fill protocol 114 and the pressure calibration protocol 116 is initiated in response to the syringe fill protocol trigger 112. Although the syringe fill protocol trigger 112 could be a signal that is automatically generated by the power injector (e.g., a signal that is generated in response to an identification that an "empty" syringe has been installed on the power injector), the syringe fill protocol trigger 112 may also require user input. In one embodiment, the syringe fill protocol trigger 112 is in the form of any appropriate data entry device or element that may be associated with a power injector that incorporates the power injector control logic 110. For instance, the syringe fill protocol trigger 112 may be in the form of a button or the like that is presented on a touch screen display or graphical user interface of a power injector (e.g., touch screen display 44 of the power injector 40). The syringe fill protocol trigger 112 may also be characterized as being presented on a touch screen display or graphical user interface of a power injector, and furthermore responsive to user input.

The syringe fill protocol 114 may be of any appropriate type, including without limitation for providing a manual fill or an automatic fill of a syringe installed on the power injector. Any appropriate step or combination of steps may be used by the syringe fill protocol 114 to provide one or more fluids to a syringe in any appropriate manner. It should be appreciated that the term "fill" in relation to the syringe fill protocol 114 is not intended to require that the entire volumetric capacity of a syringe be loaded with fluid during a syringe fill operation. Instead, the syringe fill protocol 114 may be used to provide any appropriate quantity or volume of fluid to a syringe installed on the power injector.

The pressure calibration protocol 116 is initiated in response to the syringe fill protocol trigger 112. The pressure calibration protocol 116 may be of any appropriate form and/or type, and in any case is also operatively interconnected with the pressure monitoring protocol 118. Generally, the power injector control logic 110 is configured such that the pressure calibration protocol 116 is executed for each execution of the syringe fill protocol 114 and for purposes of calibrating or updating the pressure monitoring protocol 118.

The pressure monitoring protocol 118 may be of any appropriate type, and is executed to at least in effect monitor fluid pressure during the execution of an injection protocol 120. Any appropriate step or combination of steps may be used by the pressure monitoring protocol 118, and fluid pressure may be monitored in any appropriate manner and on any appropriate basis. In one embodiment, a calibrated pressure is compared with a pressure limit by the pressure monitoring protocol 118, and this comparison may be undertaken in any appropriate manner. Any appropriate step or combination of steps may be initiated in response to the pressure monitoring protocol 118 identifying that a calibrated pressure value is greater than or equal to a pressure limit. The pressure limit may be established in any appropriate manner and may be of any appropriate value.

The injection protocol 120 may be configured to control the manner in which one or more fluids are being delivered to a fluid target, such as for injection into a patient. Generally, one or more fluids may be sequentially delivered to a fluid target, may be simultaneously delivered to a fluid target, or any combination thereof. Each discrete fluid discharge provided by the injection protocol 120 may be characterized as a phase. One or more phases may be utilized for one or multiple fluids, and the phases may be executed in any appropriate order for purposes of the injection protocol 120. Generally, the injection protocol 120 may be configured to use any appropriate number of fluids (including a single fluid or multiple fluids) and any appropriate number of phases (including a single phase or multiple phases), where each phase may deliver any appropriate fluid volume at any appropriate flow rate (including one or more fixed flow rates, one or more variable flow rates, and any combination thereof). In one embodiment, the injection protocol 120 includes at least one phase of contrast media and at least one phase of saline. For instance, the injection protocol 120 may be configured to deliver a programmed volume of contrast media at a programmed flow rate, followed by a programmed volume of saline at a programmed flow rate.

Any appropriate number of injection protocols 120 (e.g., one or more) may be stored in relation to the power injector control logic 110 and selected/retrieved in any appropriate manner. Another option is for an operator to define an injection protocol 120 to the power injector control logic 110 in preparation for initiating an injection procedure.

Figure 4:
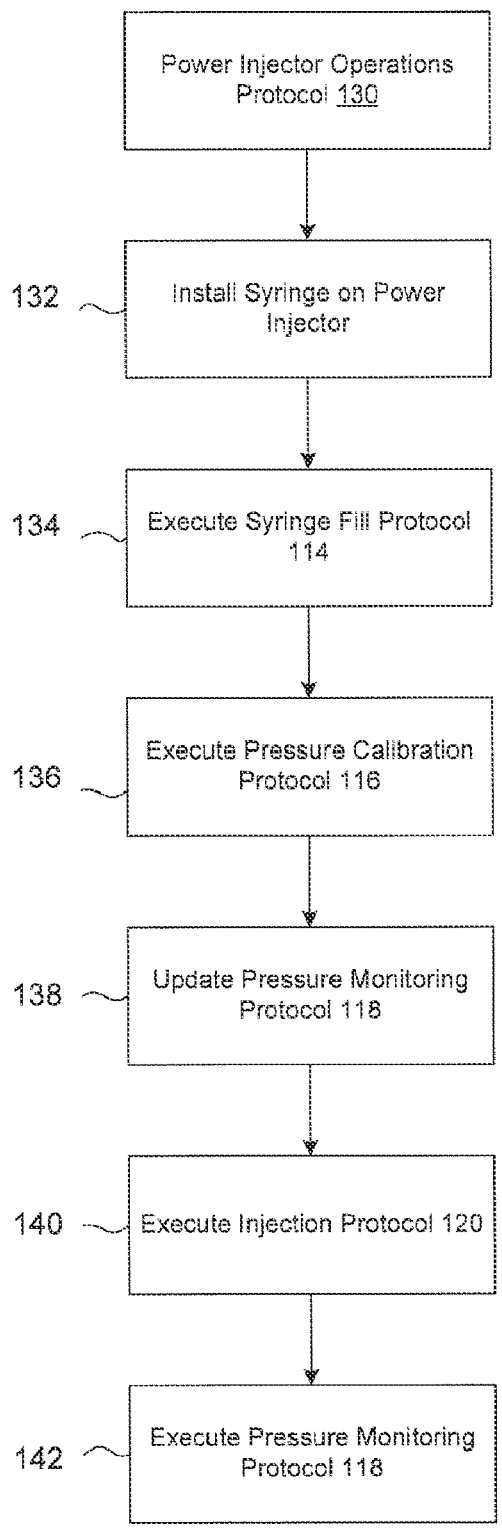
FIG. 4 is one embodiment of a power injector operations protocol that may be utilized by the power injector control logic of FIG. 3.

One embodiment of a power injector operations protocol is illustrated in FIG. 4, is identified by reference numeral 130, and may be utilized by the power injector control logic 110 of FIG. 3. The power injector operations protocol 130 includes installing a syringe on a power injector pursuant to step 132. This syringe may be of any appropriate size, shape, configuration, and/or type, and may be installed on a power injector in any appropriate manner (e.g., on a syringe mount of any appropriate size, shape, configuration, and/or type, including a syringe mount that is installed on a powerhead with tooling; on an adapter that may be installed on such a syringe mount by hand; on a faceplate that may be installed on a powerhead by hand).

A syringe fill protocol 114 is executed pursuant to step 134 of the power injector operations protocol 130, as well as a pressure calibration protocol 116 pursuant to step 136. At least parts of step 134 (syringe fill protocol 114) and step 136 (pressure calibration protocol 116) may be executed at the same time. In any case, the pressure monitoring protocol 118 is updated in accordance with step 138 and in response to the execution of the pressure calibration protocol 116 (step 136). Typically after the pressure monitoring protocol 118 has been updated (step 138), an injection protocol 120 is executed by step 140. A pressure monitoring protocol 118 is executed (step 142) during at least part of, but more typically throughout, the execution of the injection protocol 120 (step 140).

Figure 5:
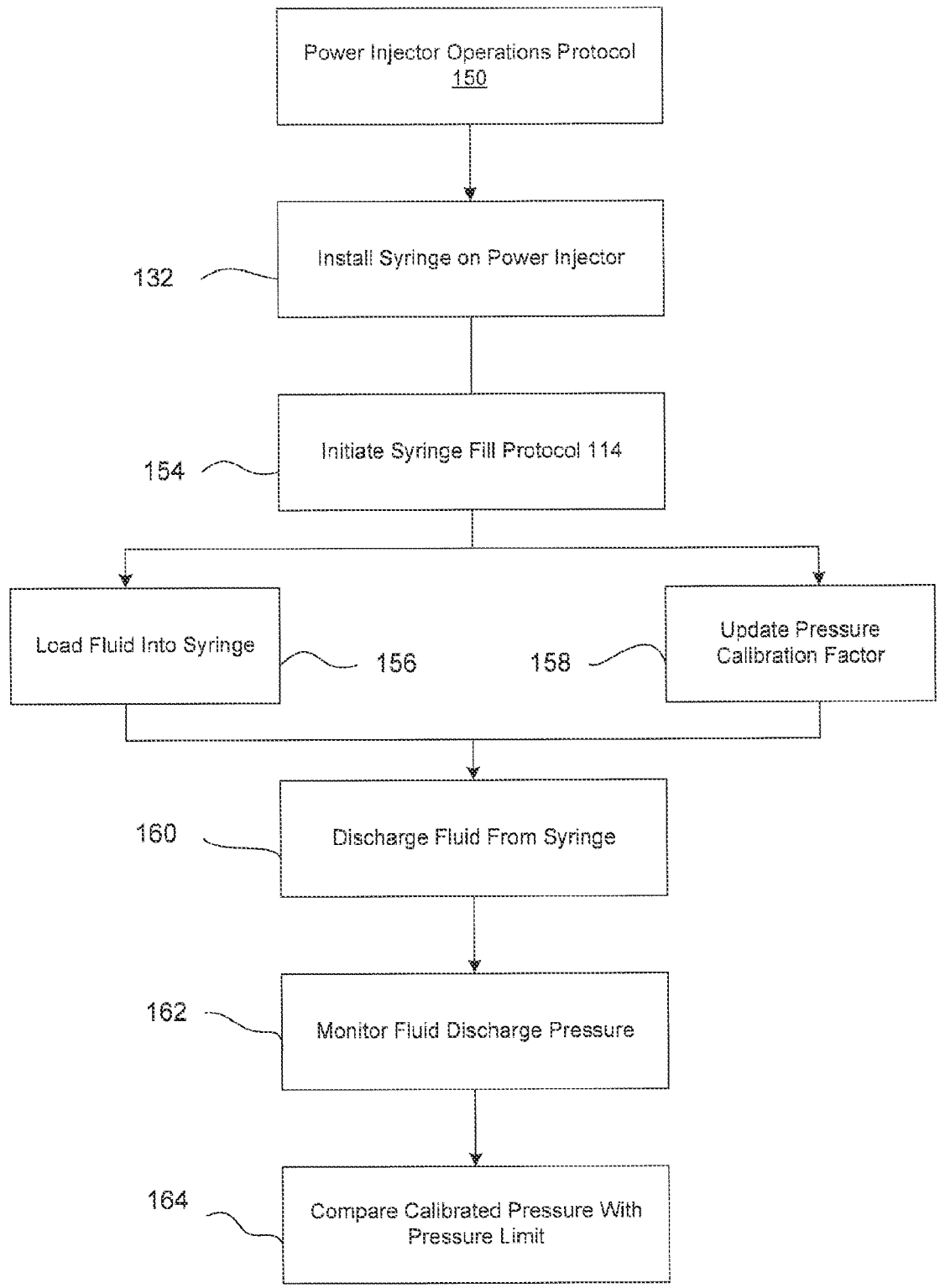
FIG. 5 is another embodiment of a power injector operations protocol that may be utilized by the power injector control logic of FIG. 3.

Another embodiment of a power injector operations protocol is illustrated in FIG. 5, is identified by reference numeral 150, and may be utilized by the power injector control logic 110 of FIG. 3. The protocol 150 includes installing a syringe on a power injector in accordance with the above-described step 132 (FIG. 4). A syringe fill protocol 114 is initiated pursuant to step 154. In this regard, fluid is loaded into the syringe pursuant to step 156, while a pressure calibration factor is updated pursuant to step 158. This pressure calibration factor (step 158) may be used by the pressure monitoring protocol 118 (FIG. 3).

Each of steps 156 and 158 is initiated in response to the execution of step 154 (initiating a syringe fill protocol 114). At least one or more aspects associated with the execution of step 156 (loading fluid) may occur at the same time as one or more aspects associated with the execution of step 158 (updating pressure calibration factor). However, it should be appreciated that one or more aspects associated with the execution of step 156 (loading fluid) may be executed prior to or after step 158 (updating pressure calibration factor) has been completed, or vice versa. In one embodiment, loading fluid into the syringe for purposes of step 156 first requires that a syringe plunger be advanced to a distal end of the syringe or toward a syringe discharge nozzle, and with no fluid being in the syringe at this time (e.g., this advancement may be part of a syringe fill protocol 114). Step 158 (updating pressure calibration factor) may utilize one or more aspects of this part of step 156. In any case, thereafter the syringe plunger may be retracted toward a proximal end of the syringe. This retraction of the syringe plunger may "draw" fluid into the syringe for purposes of step 156 and/or may otherwise allow fluid to be loaded into the syringe (e.g., via gravitational forces). Completing the retraction of the syringe plunger may be associated with the completion of step 156.

After each of steps 156 and 158 has been completed, the power injector operations protocol 150 proceeds to step 160, where fluid is discharged from the syringe. In one embodiment, this is provided by advancing the syringe plunger toward a syringe discharge nozzle. A fluid discharge pressure is monitored pursuant to step 162, A fluid discharge pressure may be monitored at any appropriate location and in any appropriate manner. In one embodiment, the fluid discharge pressure from the power injector is indirectly monitored through monitoring current of a motor being used by the power injector to advance the syringe for providing the fluid discharge of step 160. In any case, a calibrated pressure is compared with a pressure limit pursuant to step 164. This comparison may be undertaken in any appropriate manner and on any appropriate basis. In one embodiment, the "calibrated pressure" from step 164 is the monitored pressure from step 162, taking into account the pressure calibration factor from step 158.

The pressure limit associated with step 164 of the power injector operations protocol 150 may be established in any appropriate manner and may be of any appropriate value. Any appropriate step/action or combination of steps/actions may be initiated in response to the step 164 identifying that a particular calibrated pressure reading is greater than or equal to a pressure limit.

Figure 6:
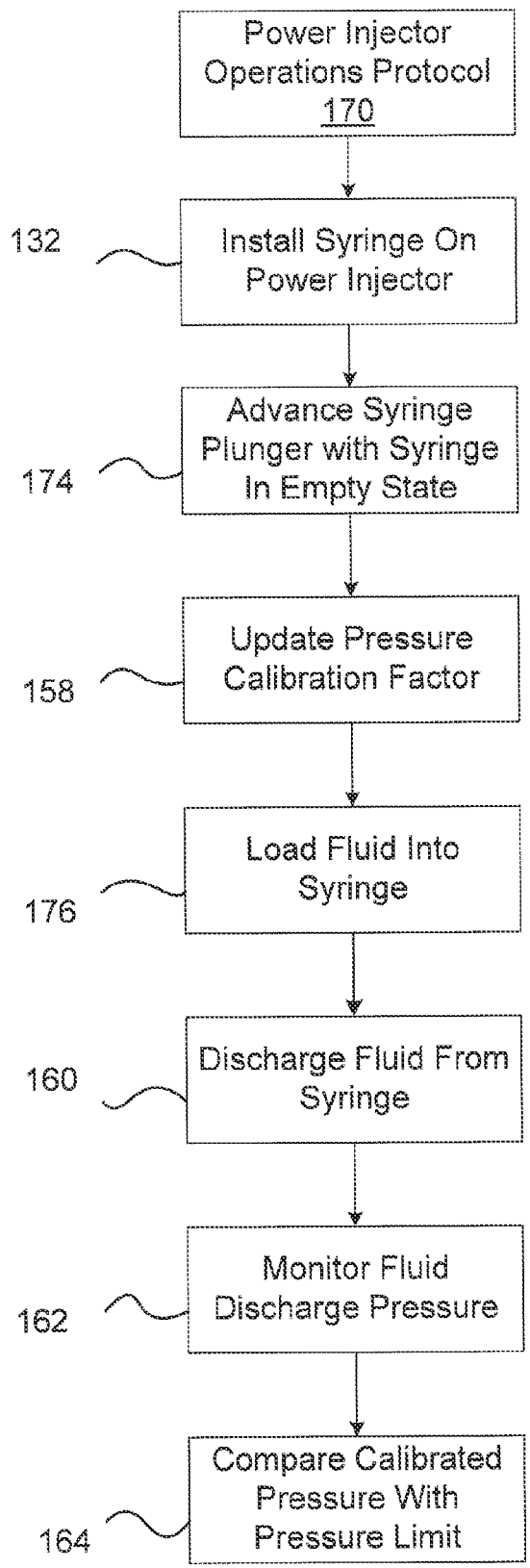
FIG. 6 is another embodiment of a power injector operations protocol that may be utilized by the power injector control logic of FIG. 3.

Another embodiment of a power injector operations protocol is illustrated in FIG. 6, is identified by reference numeral 170, and may be utilized by the power injector control logic 110 of FIG. 3. The protocol 170 includes installing a syringe on a power injector in accordance with the above-described step 132 (FIG. 4). Step 174 is directed to advancing a syringe plunger of the syringe (step 132), with the syringe being in an empty state. Step 174 may actually be part of a syringe fill protocol 114. In any case, a pressure calibration factor is updated in accordance with the above-noted step 158 (FIG. 6) and based at least in part on step 174. This pressure calibration factor may be used by the pressure monitoring protocol 118 (FIG. 3).

Fluid may be loaded into the syringe pursuant to step 176 of the power injector operations protocol 170. Step 176 may be part of a syringe fill protocol 114, and may entail retracting a syringe plunger to draw or otherwise allow fluid to be directed into the syringe. In any case and after step 176 has been completed, the power injector operations protocol 150 proceeds to the above-described step 160 (FIG. 5), where fluid is discharged from the syringe. A fluid discharge pressure is monitored pursuant to the above-described step 162 (FIG. 5). A calibrated pressure is compared with a pressure limit pursuant to the above-described step 164 (FIG. 5).

Figure 7:
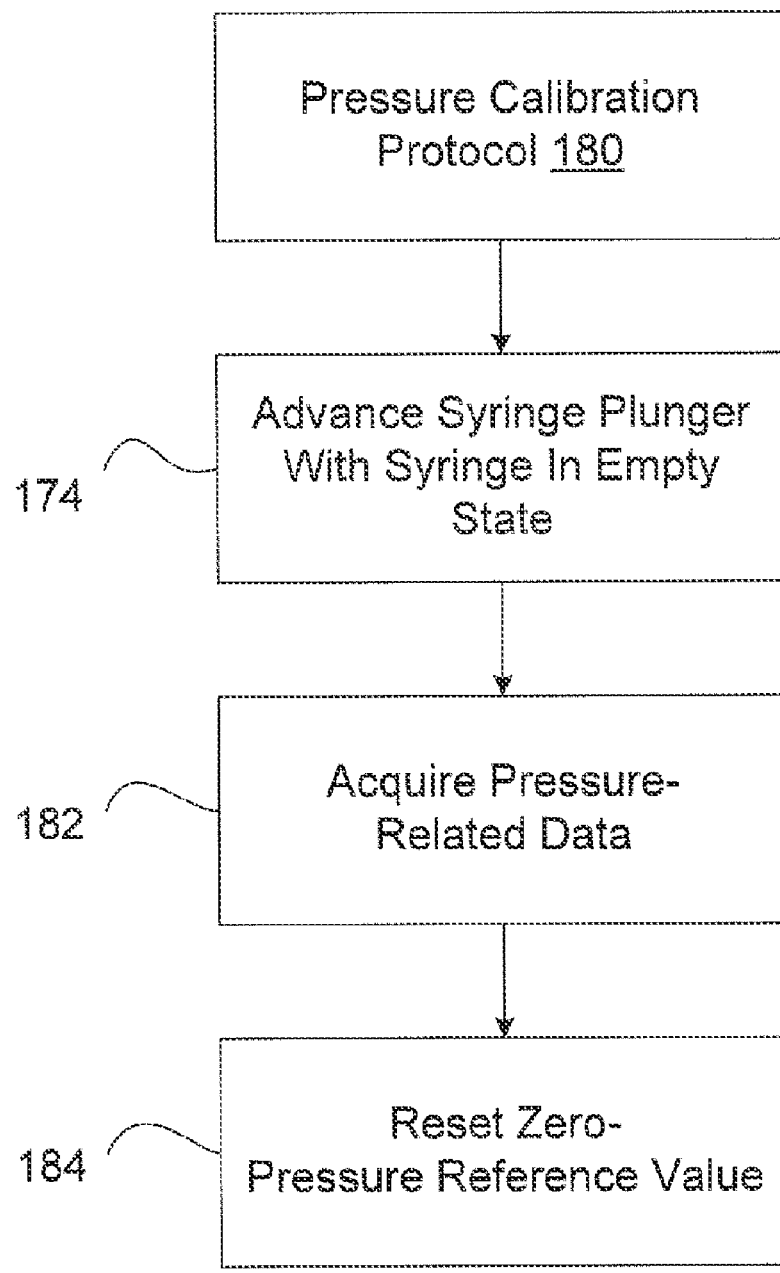
FIG. 7 is one embodiment of a pressure calibration protocol that may be utilized by the power injector control logic of FIG. 3.

The power injector operations protocols 150 and 170 of FIGS. 5 and 6, respectively, each address updating a pressure calibration factor that may be used by the pressure monitoring protocol 118 (FIG. 3). FIG. 7 illustrates one embodiment of a pressure monitoring protocol 180 that embodies updating such a pressure calibration factor. The protocol 180 includes advancing a syringe plunger with the syringe (installed on a power injector) being in an empty state in accordance with the above-noted step 174 (FIG. 6). In one embodiment, the fluid-loading step 156 of the power injector operations protocol 150 of FIG. 5 utilizes this same step 174. In any case, step 182 of the pressure calibration protocol 180 is directed to acquiring pressure-related data during the execution of step 174. For instance, step 182 may be directed to determining the amount of force required to move the syringe plunger for purposes of step 174, and this force may be equated with the above-noted pressure calibration factor. This pressure-related data may be used by step 184 to reset a zero-pressure reference value for the pressure monitoring protocol 118 (FIG. 3). For instance, this resetting of the zero-pressure reference value may entail taking into account the pressure calibration factor acquired from step 182.

Consider the case where an electric motor is used to advance a syringe plunger of a syringe installed on a power injector. The current of this motor may be used to determine the fluid discharge pressure from the syringe. That is, the magnitude of the current may be equated with a certain fluid pressure. The pressure-related data of step 182 of the pressure calibration protocol 180 may be in the form of a current value, and this current value may be subtracted from the current values that are obtained during the execution of the pressure monitoring protocol 118 (which in turn is executed during an injection protocol) to define a calibrated pressure that is compared with a pressure limit.

The power injector control logic 110, including without limitation each of its protocols, may be implemented in any appropriate manner, including without limitation in any appropriate software, firmware, or hardware, using one or more platforms, using one or more processors, using memory of any appropriate type, using any single computer of any appropriate type or a multiple computers of any appropriate type and interconnected in any appropriate manner, or any combination thereof. The power injector control logic 110, including without limitation each of its protocols, may be implemented at any single location or at multiple locations that are interconnected in any appropriate manner (e.g., via any type of network).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A method of operation for a power injector comprising:
installing a syringe on a power injector, wherein said syringe comprises a syringe plunger and is in an empty state for said installing step, wherein said installing step is repeated a plurality of times, and wherein for each execution of said installing step on said power injector, said method further comprises the steps of:
calibrating a pressure monitoring protocol, wherein said power injector comprises said pressure monitoring protocol;
loading a fluid into said syringe while installed on and using said power injector;
discharging said fluid from said syringe while installed on and using said power injector, wherein said discharging step is executed after said calibrating and loading steps; and
monitoring said discharging step using said pressure monitoring protocol.

2. The method of claim 1, wherein for each execution of said installing step, said method further comprises:
advancing said syringe plunger with said syringe being in said empty state and while installed on and using said power injector, wherein said calibrating step comprises using said advancing step.

3. The method of claim 2, wherein a fluid loading operation step for each execution of said installing step comprises said advancing step, said calibrating step, and said loading step.

4. The method of claim 2, wherein said calibrating step comprises determining a force required for said advancing step, and accounting for said force in said pressure monitoring protocol.

5. The method of claim 2, wherein said advancing step is initiated with said syringe plunger being in a fully retracted position.

6. The method of claim 2, wherein said syringe comprises a discharge nozzle, and wherein said advancing step comprises decreasing a spacing between said syringe plunger and said discharge nozzle.

7. The method of claim 2, wherein said syringe comprises a discharge nozzle, and wherein said advancing step comprises moving said syringe plunger toward said discharge nozzle.

8. The method of claim 2, further comprising retracting said syringe plunger to a fully retracted position prior to initiating said advancing step.

9. The method of claim 2, wherein said calibrating step comprises determining a magnitude of a force required for said advancing step.

10. The method of claim 9, wherein said calibrating step comprises accounting for said magnitude of said force in said pressure monitoring protocol.

11. The method of claim 9, wherein said calibrating step comprises decreasing an output of said pressure monitoring protocol by a value associated with said magnitude of said force.

12. The method of claim 2, wherein said advancing step comprises moving said syringe plunger in a first direction, wherein said loading step comprises moving said syringe plunger in a second direction, and wherein said first and second directions are opposite of each other.

13. The method of claim 1, wherein said calibrating step is executed after said installing step.

14. The method of claim 1, wherein said calibrating step is executed prior to said loading step.

15. The method of claim 1, wherein said calibrating step is executed prior to any said fluid being directed into said syringe.

16. The method of claim 1, wherein said calibrating step comprises establishing a zero-pressure reference value for said pressure monitoring protocol.

17. The method of claim 1, wherein said loading step comprises retracting said syringe plunger.

18. The method of claim 1, wherein said syringe comprises a discharge nozzle, wherein said loading step comprises increasing a spacing between said syringe plunger and said discharge nozzle.

19. The method of claim 1, further comprising:
identifying a calibrated pressure from said monitoring step and based upon said calibrating step; and
comparing said calibrated pressure with a pressure limit.

20. A method of operation for a power injector comprising:
installing a syringe on a power injector, wherein said syringe comprises a syringe plunger and is in an empty state for said installing step, wherein said installing step is repeated a plurality of times, and wherein for each execution of said installing step on said power injector, said method further comprises the steps of:
executing a fill sequence after said installing step, while said syringe is installed on said power injector, and using said power injector, said executing a fill sequence step comprising:
executing a first moving step comprising moving said syringe plunger with said syringe being in said empty state, while installed on said power injector, and using said power injector, wherein said syringe remains in said empty state throughout said first moving step;
acquiring a reference value from said first moving step; and
loading a fluid into said syringe after said installing step and after said acquiring step, said loading step comprising executing a second moving step comprising moving said syringe plunger using said power injector;
discharging said fluid from said syringe after a completion of said fill sequence, while said syringe is installed on said power injector, and comprising executing a third moving step comprising moving said syringe plunger using said power injector; and
monitoring said discharging step using said reference value associated with said fill sequence.

21. The method of claim 20, wherein said reference value is associated with a force used for said first moving step.

22. The method of claim 20, wherein said monitoring step comprises comparing a pressure from said discharging step with a pressure limit, wherein said comparing step comprises accounting for said reference value.

23. The method of claim 20, wherein said monitoring step comprises:
monitoring a pressure from said discharging step;
identifying a calibrated pressure comprising reducing said pressure from said monitoring step based upon said reference value; and
comparing said calibrated pressure with a pressure limit.

24. The method of claim 20, further comprising calibrating a pressure monitoring protocol, wherein said power injector comprises said pressure monitoring protocol, and wherein said calibrating step comprises said acquiring step.

25. The method of claim 24, wherein said first moving step comprises advancing said syringe plunger, and wherein said calibrating step comprising using said advancing step.

26. A power injector comprising:
a syringe plunger driver comprising a motorized drive source;
a syringe comprising a syringe plunger; and
power injector control logic comprising a syringe fill protocol and a pressure monitoring protocol, wherein said pressure monitoring protocol comprises a pressure calibration factor, and wherein said power injector control logic is configured to update said pressure calibration factor on each execution of said syringe fill protocol.

27. The power injector of claim 26, wherein said power injector control logic comprises a pressure calibration protocol.

28. The power injector of claim 27, further comprising a syringe fill protocol trigger operatively interconnected with each of said syringe fill protocol and said pressure calibration protocol.

29. The power injector of claim 28, wherein said syringe fill protocol trigger comprises a hand-activated device.

30. The power injector of claim 29, wherein said power injector comprises a touch screen display, and wherein said hand-activated device is presented on said touch screen display.

31. The power injector of claim 28, wherein said power injector comprises a graphical user interface, and wherein said syringe fill protocol trigger is presented on said graphical user interface and is responsive to user input.

32. The power injector of claim 27, wherein said syringe fill protocol is configured to advance said syringe plunger with said syringe being in an empty state, and wherein said pressure calibration protocol is configured to use data acquired from advancing said plunger with said syringe being in said empty state.

33. The power injector of claim 26, wherein said power injector control logic further comprises a pressure calibration protocol, wherein said pressure calibration protocol is operatively interconnected with said pressure monitoring protocol, and wherein said power injector control logic is configured to execute said pressure calibration protocol on each execution of said syringe fill protocol.

34. The power injector of claim 33, further comprising a syringe fill protocol trigger operatively interconnected with each of said syringe fill protocol and said pressure calibration protocol.

35. The power injector of claim 26, wherein said syringe fill protocol is configured to advance said syringe plunger with said syringe being in an empty state, and wherein said pressure calibration factor is based upon data acquired from advancement of said plunger by said syringe fill protocol and with said syringe being in said empty state.

* * * * *